United States Patent [19]

Baldwin et al.

[11] Patent Number: 4,879,249
[45] Date of Patent: Nov. 7, 1989

[54] LINKER COMPOUNDS, LINKER-COMPOUND-LIGANDS AND LINKER-COMPOUND-RECEPTORS

[76] Inventors: Thomas O. Baldwin, 801 Delma Dr.; Thomas F. Holzman, 807 D Nauidad, both of Bryan, Tex. 77801; Paul S. Satoh, 1424 Surrey, Portage, Mich. 49081; Frederick S. Yein, 907 Boswell La., Kalamazoo, Mich. 49007

[21] Appl. No.: 840,187

[22] Filed: Mar. 17, 1986

Related U.S. Application Data

[62] Division of Ser. No. 469,852, Feb. 25, 1983, Pat. No. 4,614,712.

[51] Int. Cl.[4] ............... G01N 33/532; C07D 213/62; C07D 209/48
[52] U.S. Cl. ..................... 436/543; 435/188; 436/544; 546/261; 548/475; 558/6; 558/15; 558/397; 558/437; 562/512; 564/500; 568/22; 560/307
[58] Field of Search ............... 436/543, 544; 435/188; 546/261; 568/22; 562/512; 548/475; 260/544 S; 558/6, 397, 437, 15; 564/500

[56] References Cited

U.S. PATENT DOCUMENTS

| | | | |
|---|---|---|---|
| 4,080,399 | 3/1978 | Uhrhan | 548/475 X |
| 4,231,999 | 11/1980 | Carlsson | 436/518 |
| 4,237,267 | 12/1980 | Okuyama | 435/194 X |
| 4,244,950 | 1/1981 | De Ridder | 546/261 X |
| 4,287,345 | 9/1981 | Kotani | 546/261 |
| 4,347,366 | 8/1982 | D'Amico | 546/261 |
| 4,380,581 | 4/1983 | Boguslaski | 435/7 |
| 4,643,994 | 2/1987 | Block | 568/22 X |
| 4,647,655 | 3/1987 | Axen | 546/261 |
| 4,722,749 | 2/1988 | Lee | 546/261 X |

OTHER PUBLICATIONS

Johnston, T. P. et al., J. Org. Chem., 26, 3780–3783, (1961).

*Primary Examiner*—Sidney Marantz

[57] ABSTRACT

Novel immunoassay which utilizes an enzyme linked ligand or receptor wherein the enzyme is bacterial luciferase; mercantile kit useful in performing said immunoassay; and compounds utilized in performing said assay.

2 Claims, No Drawings

LINKER COMPOUNDS, LINKER-COMPOUND-LIGANDS AND LINKER-COMPOUND-RECEPTORS

This is a divisional application of Ser. No. 469,852, filed Feb. 25, 1988, now U.S. Pat. No. 4,614,712, issued Sept. 30, 1986.

FIELD OF INVENTION

The present invention is an enzyme-linked immunoassay and components utilized in said immunoassay.

DESCRIPTION OF PRIOR ART

Immunoassays wherein one of the immunological components, e.g., either the antigen or the antibody, is labeled with a radioactive isotope tracer have an established significant role in medical diagnosis and in the detection of toxins and other substances in industrial environments. More recently much attention has been focused on assay systems which use labels of a non-radioactive nature, such as chemi-luminescent agents, fluorescent agents and enzymes. Various types of enzyme-labeled or enzyme-linked assays have been described in the literature. For example, U.S. Pat. No. 3,654,090 describes an assay wherein one of the two immunological components is covalently linked to an enzyme and the other said component is utilized in an insolubilized form, and following incubation with the test sample the enzyme-labeled component in either the solid or liquid phase is a measure of the amount of component in the sample.

In U.S. Pat. No. 3,817,837 there is described a means of detecting substances or ligands for which receptors, e.g., antibodies, can be generated or occur naturally which comprises reacting in an aqueous medium a soluble enzyme-bound ligand, a receptor for the ligand and the substance to be assayed. In this enzyme-linked assay, binding of the receptor to the enzyme-bound ligand results in a substantial reduction in the enzyme activity. Thus, changes in enzyme activity in the assay medium affords a means of measuring the quantity of ligand in the assay sample. It is important to note that the enzyme in this particular enzyme-bound ligand complex retains its activity whereas once the receptor binds the enzyme-bound ligand complex the enzyme is rendered inactive substantially. A similar enzyme-linked assay is described in U.S. Pat. No. 4,039,385.

U.S. Pat. No. 4,171,244 describes an assay for thyroid hormones which utilizes an enzyme-bound complex wherein the enzyme loses about 50% or more of its activity upon forming the complex but which regains a portion of this lost activity when bound to a receptor in the assay procedure. Again changes in enzyme activity in the assay medium provide a means of measuring the quantity of ligand, i.e., thyroid hormone, in the assay sample.

In U.S. Pat. No.4,231,999 there is described a modification of the enzyme-linked assay system of U.S. Pat. No.3,817,837. In the method of the biospecific affinity reaction described in the '999 patent one of the components of said reaction is linked to the label, e.g., an enzyme, by a splittable bond of a covalent nature. Although the enzyme activity is reduced substantially by the biospecific affinity reaction, release of the enzyme by splitting the covalent bond optimizes enzyme activity for assay purposes. Although there is an indication that various splittable bonds may be employed, the splittable bond of choice in the '999 patent is the disulfide linkage, i.e., the label, e.g., enzyme and one of the components of the affinity reaction are linked together by a disulfide bridge. The generation of such a disulfide linkage requires the presence of thiol groups in the label and affinity reaction component, and the '999 patent describes means whereby such groups may be introduced. However, there does not appear to be any. Convenient or specific means whereby the number of thiol groups introduced into, e.g., an enzyme label may be controlled which factor could ultimately interfere with or decrease the sensitivity of the assay.

Other types of enzyme-linked assay systems are described in U.S. Pat. Nos. 4,277,560, 4,281,061, and 4,233,402. An article by B. R. Clark and E. Engvall entitled Enzyme Linked Immunosorbent Assay (ELISA): Theoretical and Practical Aspects in "Enzyme-Immunoassay", E. T. Maggio, ed., CRC Press, Inc., Boca Raton, FL (1980), pp. 167–179, describes the basic aspects of enzyme linked immunoassays.

The present invention provides an enzyme-linked assay system wherein the enzyme is bacterial luciferase.

Bacterial luciferase is a flavin-linked monooxygenase (hydroxylase) which catalyzes the bioluminescent oxidation by $O_2$ of reduced flavin mononucleotide and a long-chain fatty aldehyde depicted below to yield FMN, the corresponding fatty acid, blue-green light and water (M. M. Ziegler and T. O. Baldwin, Current Topics in Bioenergetics, Vol. 12, pp. 65–113 (1981)).

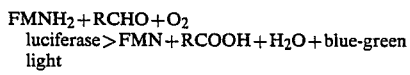
$FMNH_2 + RCHO + O_2$
luciferase $>$ FMN + RCOOH + $H_2O$ + blue-green light The luciferase protein is an $\alpha\beta$ dimer with a single center confined primarily, if not exclusively, to the $\alpha$ subunit. The precise role of the $\beta$ subunit is not clearly understood, but it is required for bioluminescence activity. Detailed chemical modification studies reported in a series of papers during the past ten years show that the luciferase of the luminous marine bacterium Vibrio harveyi possesses one particularly reactive sulfhydryl (cysteinyl) group (one of about 15) that is located on the $\alpha$ subunit in or near the active center which when modified with any of a variety of reagents renders the enzyme completely inactive (Ziegler and Baldwin, 1981, ibid.). This reactive cysteinyl residue resides in a hydrophobic cleft (M. Z. Nicoli and J. W. Hastings, J. Biol. Chem. 249, 2393–2396 (1974) and Merritt and Baldwin, Arch. Biochem. Biophys. 202, 499–506 (1980). The apparent second order rate constant for the inactivation of luciferase with a series of N,n-alKyl maleimides shows a marked chain length effect, apparently due to binding of the hydrophobic alkyl chain in the hydrophobic cleft prior to covalent reaction with the reactive cysteinyl residue.

Another class of compounds, the alkylalkanethiolsulfonates, has been used to modify the luciferase. Two interesting observations came from these studies. First, modification of the reactive thiol with as small a group as the $-SCH_3$ rendered the enzyme inactive (M. M. Ziegler and T. O. Baldwin (1981) in "Bioluminescence and Chemiluminescence: Basic Chemistry and Analytical Applications" (M. A. DeLuca and W. D. McElroy, eds.) Academic Press, New York, pp. 155–160). Second, the mixed disulfide that results from reaction between luciferase and the thiolsulfonate was readily reduced by $\beta$-mercaptoethanol, dithiothreitol, or other reducing agent resulting in quantitative recovery of bioluminescence activity (W. R. Welches and T. O. Baldwin, Biochemistry 20, 512–517 (1981)). These characteristics of bacterial luciferase render the enzyme uniquely adaptable for the present invention.

SUMMARY OF THE INVENTION

The present invention is a method of assaying for substances using an enzyme-linked assay system wherein the enzyme is bacterial luciferase. Bacterial luciferase can be used as a label or as an analytically indicatable group in assaying for substances by substantially any of the known assay methodologies utilizing reciprocal binding pair members which exhibit biospecific affinity for one another. The present invention is unique from other known enzyme linked immunosorbent assays involving biospecific affinity reactions of reciprocal binding pair members in that the enzyme, i.e., bacterial luciferase, is linked to one of said binding pair members in such a manner that the enzyme is completely inactivated, and following the various biospecific affinity reactions involved in the assay the enzyme activity is completely restored upon breaking the link enabling one to measure said enzyme activity for assay purposes. The bacterial luciferase is linked to one of said reciprocal binding pair members by a splittable bond of a covalent nature.

For purposes of convenience the reciprocal binding pair members are referred to herein as ligand or ligands, i.e., the substance being measured or assayed, and receptor or receptors, i.e., the compound or substance having a binding affinity for a ligand. Although the terms ligand and receptor are used herein in the capacity just defined it is understood that in some instances the substance to be assayed or measured, i.e., the ligand, is in fact a receptor. The label, i.e., bacterial luciferase, is reversibly linked to either the ligand or the receptor, forming a luciferase labeled ligand or a luciferase labeled receptor, and in the performance of the assay changes in the number of quanta of light emitted by the enzyme provides a means of measuring levels of substances being assayed. Typically the assay is carried out in any of a variety of well-known manners such as competitive affinity binding, displacement or disequilibration or using immunometric procedures.

Thus, the present invention provides a method for quantitating the presence of a substance, herein referred to as ligand, in a medium which comprises incubating said medium, a known amount of a luciferase labeled ligand, and a known amount of a receptor capable of binding said ligand and luciferase labeled ligand; separating the receptor bound material from the unbound material; activating the luciferase in the receptor-bound material and/or unbound material; and measuring the luciferase activity. This assay procedure can be carried out in either the solid or liquid phase, i.e., either one of the binding pairs may be immobilized by being affixed to a solid surface such as beads or a test tube, or all components may remain in solution. When performing the assay in the solid phase the binding pair member which is immobilized will be the unlabeled binding pair member. This competitive type assay may be modified such that the receptor carries the label, thus the assay medium comprises the sample or unknown medium being assayed, a known amount of luciferase labeled receptor, and a known amount of immobilized ligand which is the same ligand as that which is being assayed. Additionally, the competitive type assay may be performed by incubating the medium containing the sample being assayed, a known amount of immobilized ligand, and a known amount of unlabeled receptor capable of binding said ligand. Following incubation the solid or immobilized phase is separated from the liquid phase and a second receptor carrying the luciferase label is added to the immobilized phase. The second receptor is capable of binding the first or unlabeled receptor. The medium containing the second receptor is incubated then the phases are separated, the luciferase activated and enzyme activity measured.

Further, the present invention provides a method for quantitating the presence of a ligand in a medium which comprises combining said medium with an equilibrated composition comprising binding equivalent quantities of a known amount of luciferase labeled ligand and a known amount of a receptor capable of binding said ligand and said luciferase labeled ligand; incubating the resulting combination; separating the receptor-bound material from the unbound material; activating the luciferase in the receptor-bound material and/or the unbound material; and measuring the luciferase activity. This displacement type assay may also be carried out in such a manner that the receptor is either immobilized or remains soluble during incubation.

This invention also provides a means of carrying out an immunometric assay for determining the presence of a ligand in a medium which assay may be a two-site or a single-site type assay. Thus there is provided a means for determining the presence of a ligand in a medium which comprises incubating a known amount of a luciferase labeled receptor capable of binding said ligand and an equilibrated composition comprising said medium and a known amount of an unlabeled receptor capable of binding said ligand; separating the bound luciferase labeled receptor material from the unbound luciferase labeled receptor material; activating the luciferase in the bound material or the unbound material; and measuring the luciferase activity. The unlabeled receptor is the same as the receptor contained in the luciferase receptor complex. This assay also may be carried out in a solid or liquid phase, i.e., the unlabeled receptor is either immobilized or remains soluble in the assay medium.

This two-site immunometric type assay may be modified by using a second receptor. Thus there is provided a means for determining the presence of a ligand in a medium which comprises incubating said medium and a known amount of an immobilized first receptor capable of binding said ligand; adding excess of a second receptor capable of binding said ligand said second receptor being from an animal species different from the animal species in which the first receptor is elicited, and incubating the resultant composition; separating the immobilized phase from the liquid phase; adding a known amount of a luciferase labeled receptor capable of binding said second receptor and incubating the resultant composition; separating the immobilized phase from the liquid phase; activating the luciferase in the immobilized phase or the liquid phase; and measuring the luciferase activity.

The above-described two-site immunometric assays are employed when assaying for ligands which have more than one antigenic determinant.

The single-site immunometric type assay can be performed in two different manners. Illustratively, the medium containing the ligand to be assayed is incubated with a known amount of an immobilized receptor capable of binding said ligand after which the immobilized phase is separated from the liquid phase. A known amount of a luciferase labeled ligand is then added to the immobilized phase and the resultant composition is incubated. Following the second incubation the immobilized phase is separated from the liquid phase, the luciferase is activated in one or the other or both of these phases, and the enzyme activity is measured. Alternatively, there is incubated a known amount of an immobilized ligand and an equilibrated mixture of said medium containing the ligand to be assayed and a known amount of a luciferase labeled receptor capable of binding said ligand. Following incubation the immobilized and liquid phases are separated, the luciferase in either the immobilized or liquid phase (or both) is activated, and the enzyme activity is measured.

In the foregoing description of immunoassay procedures in any particular procedure when reference is made to a known amount of a ligand or a luciferase labeled ligand, that phase means the purified form (either unlabeled or luciferase labeled) of the substance, i.e., ligand, being assayed.

This invention also provides a mercantile kit containing reagents useful in performing assays of the present invention which comprises multiple containers wherein one of said containers has therein luciferase labeled ligand said ligand of which is a purified form of the ligand to be assayed, and another of said containers has therein a receptor capable of binding said ligand which receptor optionally may be immobilized. Also there is provided a mercantile kit useful in performing immunoassays of the present invention which comprises multiple containers wherein one of said containers has therein luciferase labeled receptor said receptor being capable of binding the ligand to be assayed, and another of said containers has therein either an immobilized ligand said immobilized ligand being a purified form of the ligand to be assayed, or has therein unlabeled receptor capable of binding said ligand to be assayed. There is further provided a mercantile kit useful in the performance of immunoassays of the present invention which comprises multiple containers wherein one of said containers has therein a quantity of immobilized ligand said immobilized ligand being a purified form of the ligand to be assayed, another of said containers has therein a quantity of unlabeled receptor capable of binding said ligand, and another of said containers has therein a quantity of luciferase labeled receptor said receptor being capable of binding the unlabeled receptor. Additionally there is provided a mercantile kit useful in performing assays of the present invention which comprises multiple containers one of said containers having therein a quantity of immobilized receptor capable of binding the ligand to be assayed, another of said containers has therein a second receptor capable of binding the ligand to be assayed said second receptor being from an animal species different from the animal species in which the immobilized receptor is elicited, and another of said containers has therein a quantity of luciferase labeled receptor said receptor being capable of binding said second receptor.

DETAILED DESCRIPTION OF INVENTION

In practicing the present invention the bacterial luciferase is reversibly linked to either the ligand or the receptor to form a luciferase labeled ligand or a luciferase labeled receptor. Any reference herein to luciferase means bacterial luciferase. Bacterial luciferase from any species capable of producing said enzyme may be employed, e.g., luminous bacteria or any mutant thereof.

In forming the luciferase labeled ligand or the luciferase labeled receptor, the ligand or receptor is reacted with a bifunctional linker compound to give a linker compound-ligand intermediate or a linker compound-receptor intermediate. The thus formed intermediates are brought together and bound to bacterial luciferase by a reversible or cleavable covalent linkage. This covalent binding of the intermediates and bacterial luciferase renders the enzyme inactive while the ligand or receptor is available to bind its counterpart. Upon cleaving the covalent linkage the luciferase activity is restored and the concentration of ligand being assayed can be determined by measuring the luminescence.

The substances to be measured or detected in the performance of the assay, i.e., the ligand, includes those substances which are antigenic or can be rendered antigenic, i.e., haptens, or which have naturally occurring receptors. Reference is made to U.S. Pat. No. 3,817,837 wherein the foregoing categories of ligands are defined and exemplified. The ligands to be assayed can be substantially any of the substances which are recognized in the art as being detectable by assay procedures known heretofore or for which a receptor naturally exists or can be prepared. Thus, the ligands to be assayed by the methods of the present invention include, for example, those substances described in U.S. Pat. Nos., 3,817,837 (columns 6–26); 4,039,385 (columns 1–3); 4,108,975 (column 5); 4,191,613 (columns 4–8); 4,235,960 (columns 3–4); and 4,233,402 (columns 10–16). It is necessary, however, that the ligand be capable of, or can be modified to render it capable of, reacting with the bifunctional linker compounds. More specifically, the ligands to be assayed include steroids, such as dihydrotestosterone, aldosterone, estradiol, estrone, estriol, dehydroepiandroster-one-S (DHEA-S), cortisol, corticosterone, deoxycortisol, deoxycorticosterone, progesterone, pregnanediol, male testosterone, female testosterone, androstenedione, and 17-hydroxyprogesterone; cardiac glycosides, such as, digitoxin, digoxin and gitalin; cannabinoids, such as, tetrahydrocannabinols; opiates including morphine and the baine; peptide hormones, such as, leutinizing hormone, follicle stimulating hormone, thyroid stimulating hormone, human growth hormone, human growth factor ACTH, glucagon, insulin, human placental lactogen, prolactin, human chorionic gonadotropin, gastrins, C-peptide of insulin, folate, intact parathyroid stimulating hormone or the C-terminal thereof, and N-cholylglycine; prostaglandins and related substances, such as, $PGA_1$, $PGA_2$, $PGD_2$, $PGE_1$, $PGE_2$, $PGF_1$, $PGF_2$, thromboxane $B_2$, 6-keto $PGF_{1\alpha}$, the 6, 15-diketo-dinor derivative of $PGF_1$, $PGF_2$, $PGE_2$ and $PGE_1$, the 13, 14-dihydro-15-keto derivative of $PGF_1$, $PGF_2$, $PGE_1$ and $PGE_2$; and bicyclic forms of the 13, 14-diydro derivative of 15-keto-$PGE_2$ and 15-keto-$PGF_{2a}$; vitamins, such as, vitamin B-12, folic acid, and vitamin A; neuro-transmitters or bioactive amines, such as, norepinephrine, dopamine, and epinephrine; nucleic acids; tumor markers, such as, alpha fetoprotein, carcinoembryonic antigen (CEA), and prostatic acid phosphates; drugs, such as, acetomenophen, N-acetylprocainamide, amikacin, acetazolamide, amobarbitol, butabarbitol, chloramphenicol, carisoprodol, carbamazepine, chlorazepate, disopyramide, diazepam, dioxepin, ethosuximide, ethclorvynol, gentamicin, glutethimide, kanamycin, lidocaine, librium, meprobamate, methaqualone, methpyrlon, mephenytoin, norpropoxyphene, phenobarbital, phenytoin, procainamide, primidone, pentobarbitol, quinidine, secobarbitol, theophylline, tobramycin, thoridazine, valproic acid, vetilmicin, imipramine, amitriptyline, desipramine, nortriptyline, propranolol, thorazine, fluorazepam, clonazepam, alprazolam, valium and propoxyphene; proteins, such as, thyroid binding globulin, ferritin, myoglobin, and thyroglobulin, IgG, IgA, IgM, IgE, antitrypsin, rheumatoid factor, factor VIII, myelin basic protein, cross reactive protein, complement factors $C_3$, $C_4$ and activated complement components $C_{3a}$, $C_{4a}$ and $C_{5a}$; enzymes, such as, resin, angiotensin I, malic dehydrogenase, pyruvic kinase, glucose 6-phosphate dehydrogenase, lactic dehydrogenase, creatine phosphokinase, and pepsinogen; nonsteroidal hormones, such as, thyroxine-4 ($T_4$) and 3,5,3-triiodothyronine; and chemical mediators such as, cyclic AMP; viral antigens resulting in, e.g., herpes simplex, hepatitis B, rubella, and rabies as well as antibodies to such antigens; antibacterial antibodies, such as, antigonococcus; parasite antigens resulting in toxoplasmosis, malaria, schistosomiasis, trypanosomiasis and syphilis and antibodies thereto.

The term receptors as used herein includes solution receptors found or generated in the plasma or cytoplasm such as antibodies, which may be naturally occurring or induced by well known procedures, cytosol, testosterone binding globulin (TEBG), trans cortin, or enzymes. Also the term receptors includes cell-bound receptors such as those for acetylcholine, catecholamines, insulin, estrogen, progesterone, testosterone and T-cell and B-cell markers. The formation and isolation of the receptors is well known in the art, e.g., see E, V. Jensen, et al., Receptors for Reproductive Hormones (B. W. O'Malley, A. R. Means, eds.), p. 60, Plenum Press, New York, London, 1973; W. I. P. Mainwarning, et al., ibid., p. 197; G. E. Block, et al., Ann. Surg. 182, 342, 1975; F. Suzuki, et al., Endocrinology, 90, 1220 (1972); R. E. Cone, "The Search for the T Cell Antigen Receptor," Progress in Immunology III, Australian Acad. of Sci., pp. 47–57, 1977.

The linker compounds employed in forming the luciferase labeled ligand or the luciferase labeled receptor can be any bifunctional compound which contains as one of the functional moieties a reactive group such as carboxyl or a reactive derivative thereof or an amino group or other reactive moiety designed to react with the ligand or receptor and contains as the other functional moiety a sulfide or sulfoxide group which will react with the reactive sulfhydryl of luciferase. The linker compound is designed to deliver the ligand or receptor to the active sulfhydryl of luciferase, and hold the ligand or receptor in position to achieve recognition and binding by its counterpart then upon appropriate treatment release the luciferase. Particularly useful as linker compounds are the compounds of Formulas I and II depicted in the Formula Chart.

The linker compounds are of two classes represented by Formulas I and II. In Formulas I and II RI is any group which will render the sulfur to which it is attached electron deficient, i.e., $R_1$ is an electron withdrawing group such as 2-benzothiazolyl, 2-pyridyl, 4pyridyl, 5-nitro-2-pyridyl, 2-pyridyl-N-oxide, or a carbonate, i.e.,

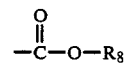

wherein $R_8$ is any ester forming group such as lower alkyl or benzyl or phenethyl.

$R_7$ can be substantially any group which will not interfere with the reaction of the sulfoxide compound with luciferase; typically $R_7$ is a lower $C_{1-6}$ alkyl group, e.g., methyl or ethyl or an aromatic group such as phenyl, substituted phenyl such as p-fluorophenyl or p-nitrophenyl or lower $C_{1-4}$ alkyl substituted phenyl 2- or 4-pyridyl; n is zero to 15, preferably zero to 4; $R_6$ is COOH; COO-succinimide; —COCl; —COBr; Cl; Br; SCN; $NH_2$;

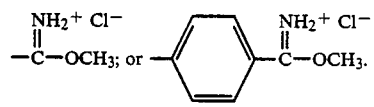

$R_2$ and $R_3$ are the same and are hydrogen, methyl, or ethyl; $R_4$ and $R_5$ are the same and are hydrogen, methyl, or ethyl; or $R_2$, $R_3$, $R_4$ and $R_5$ taken together with the carbon atoms to which they are attached represent a cycloalkyl group having from 4 to 6 carbon atoms, or represent 1,4-phenylene.

The compounds of general Formula I are known in the art or are prepared by procedures well known in the art as set forth, for example, in U.S. Pat. Nos. 4,149,003; 4,232,119; 4,175,073; 4,258,193; and 4,187,345 as well as S. J. Brois, et al., J. Am. Chem. Soc. 92, 76297631 (1970); J. E. Dunbar and J. H. Rogers, J. Org. Chem. 31, 2842–2846 (1966); and L. Field and P. M. Giles, J. Org. Chem., 309–313 (1971).

The compounds of Formula II wherein $R_7$ is methyl or p-methylpheny, n is zero, each of $R_2$, $R_3$, $R_4$, and $R_5$ is hydrogen $R_6$ is $NH_2$ are known in the art. The compounds of Formula II other than the two aforedescribed compounds are a part of the present invention.

The compounds of Formula II are prepared by procedures generally known in the art. Illustratively, a derivative of the formula $R_7SO_2SK$ prepared as generally described by Boldyner and Zakharchuk, Dokl. Akad. Naak. SSR 95, 877 (1954) is reacted with a compound of Formula III wherein n, $R_2$, $R_3$, $R_4$ and $R_5$ have the meanings defined in Formula II and $R_g$ is —COOH, Cl, Br, SCN, $NH_2$, CN or 4-cyanophenyl, by the general procedure described by Johnston and Gallagher, J. Org. Chem. 26, 3780 (1961). The nitrile derivatives obtained by the foregoing are used to prepare the carboxy imidates of Formula II by the general procedure described in U.S. Pat. No. 4,237,267. The nitrile intermediates are also a part of the present invention. The compounds of Formulas I and II wherein $R_6$ is —COO—succinimido are prepared by treating the corresponding carboxylic acid with N-hydroxysuccinimide as generally described, for example, in U.S. Pat. No.4,237,267. Compounds of Formulas I and II wherein $R_6$ is —COCl or —COBr are prepared by, e.g., treatment of the corresponding carboxyl derivative with thionyl chloride or thionyl bromide by procedures known in the art.

The compounds of Formula III are known in the art or are prepared by procedures generally known in the art.

The compounds of Formulas I and II wherein $R_6$ is —COOH or $NH_2$ are preferred for use in preparing the luciferase labeled ligand and luciferase labeled receptor of the present invention.

The bacterial luciferase employed in the present invention is isolated and purified by means known in the art, e.g., as described by Holzman and Baldwin, Biophysical Journal 33, 255 (1981).

In preparing the luciferase labeled ligand and the luciferase labeled receptor the ligand or the receptor is brought together with a linker compound of Formula I or II to effect a reaction between the group designated Rs of said compound and the ligand or receptor. The linker compound chosen depends on the nature of the reactive function present on the ligand or receptor. If the ligand or receptor does not have present thereon a suitable function for reaction with the Rs group of the compounds of Formula I or II then such function is introduced by various procedures known in the art. Also if the ligand or receptor to be assayed or to be labeled with bacterial luciferase contains any reactive sulfhydryl groups it is important that they be blocked prior to reaction with a compound of Formula I or II, or assaying, by treatment, for example, with iodoacetamide or N-ethylmaleimide.

It is apparent that the compounds of Formulas I and II will react with a variety of functional groups commonly present on, or which can be introduced into, the ligands or receptors to be labeled. Thus, compounds of Formula I or II wherein Rs is a carboxyl, a carboxysuccinimide, or an acyl chloride or acyl bromide group will react with primary amine groups forming an amide linkage. See, J. C. Sheehan and G. P. Hess, J. Am. Chem. Soc. 77, 1067 (1955); N. F. Albertson, Organic Reactions 12, 205 (1962); R. Paul and G. W. Anderson, J. Org. Chem. 27, 2094-2099 (1962); J. C. Sheehan amd P. A. Cruickshank, J. Org. Chem. 26, 2525 (1961); J. C . Sheehan, et al., J. Am. Chem. Soc. 87, 2492 (1965). Compounds of Formulas I and II wherein Rs is Br or Cl will react with primary or secondary amines present on the ligand or receptor to be labeled forming an alkyl amine linkage. Also compounds of Formulas I and II wherein $R_6$ is Br or Cl will react with carboxyl groups present on the ligand or receptor to form an ester linkage. Also a compound wherein $R_6$ is —COOH will react with a chlorine or bromine moiety which may be present on a ligand to form an ester linkage. Compounds of Formulas I and II wherein $R_6$ is SCN are useful in reacting with amine groups which may be present on the substance to be labeled forming a thiocarbonate linkage. Compounds of Formulas I and II wherein $R_6$ is $NH_2$ are useful in reacting with carboxyl groups present on the ligand or receptor forming an amide bond. Also, compounds of Formulas I and II wherein $R_6$ is $NH_2$ will react with aldehydes present on the ligand or receptor undergoing a Schiff base formation. Compounds of Formulas I and II wherein $R_6$ is a carboxymethoxime or a phenylcarboxymethoxime group are useful in reacting with amine groups present on the ligand or receptor to be labeled forming an aminoimidate linkage. Compounds of Formulas I and II wherein $R_6$ is $NH_2$ and each of $R_2$, $R_3$, $R_5$ and $R_5$ is hydrogen tend to decompose after about three days at room temperature. Therefore, these compounds should be used preferably within a day or two following preparation.

Many ligands or receptors to be labeled will contain a suitable functional group capable of reacting with the $R_6$ moiety of the compounds of Formulas I and II. For example, protein and peptide type ligands or receptors will contain amine and/or carboxy groups suitable for reaction with compounds of Formulas I and II. Prostaglandins generally will contain a carboxy group suitable for reaction or can be derivatized to render said compound suitable for reaction by means known in the art. Either the carboxyl or amine present on thyroxine and triodothyronine are suitable for reacting with compounds of Formulas carbamazepine, gentamicin, elipten, kanamycine, meprobamate, desipramine, valproic acid, chlorazepate, ethosoximide, propranolol, etc., will contain amine, carboxyl or other groups which can be utilized in producing the linker compound-ligand intermediate. Other ligands will require some modification. For example steroids and cardiac glycosides containing hydroxyl groups can be treated with phosgene to give a chlorocarbonate which can be reacted with an amine of Formula I or II; or the hydroxyl can be derivatized using succinic anhydride to give an acid moiety suitable for reaction. Hydroxymethyl groups present in, e.g., corticosteroids, can be used to form hemisuccinates suitable for reaction. Also carbonyl moieties present at various ring positions can be derivatized using O-(carboxymethyl)hydroxylamine as described by B. Erlanger, et al., J. Biol. Chem. 228, 713 (1957). Hydroxyl groups present in cannaboids and various drugs, e.g., chloramphenicol, can be utilized in a manner similar to that described for steroids to give a suitably derivatized ligand. Hydroxyl groups can be introduced into aliphatic chains (see Chinn, "Selection of Oxidants in Synthesis,", pp. 7–11, Marcel Dekker, Inc., New York, 1971 and Lee, in Augustine, "Oxidation," vol. 1, pp. 2–6, Marcel Dekker, Inc., New York, 1969) then derivatized as described above which provides a means of derivatizing, e.g., barbiturates such as pentobarbital and secobarbital, and retaining the immunogenicity of the ligand. Compounds such as diazepam, methaqualone, mephenytoin, reticillin, norpropoxyphene, phenobarbital, and pyrimidone can be derivatized by introducing a nitro group into an aromatic ring thereof then either reducing the nitro group to an amine or oxidizing the nitro group to a carboxyl group via the nitrile by means generally known in the art. Of course compounds already containing nitro groups, e.g., nitroazepam, could be reduced to amines to provide a suitable coupling moiety. Ligands containing carbohydrate moieties can be treated with periodate oxidizing the ring hydroxyls to aldehydes which can be reacted with amines of Formulas I and II by Schiff base condensation. Also, treatment with epichlorohydrin will give an epoxide derivative suitable for reacting with a diamine. See R. Axen, et al., J. Acta Chem. Scand., B-29, 471 (1975). The thus formed primary amine function can be utilized to link the ligand to a suitable compound of Formula I or II. Various other means suitable for introducing suitable reactive functions into ligands will be apparent to those skilled in the art.

In reacting the ligand or receptor with the linker compound the quantity of reactants employed will vary depending on the nature of the receptor or ligand and the number of reactive functions present thereon. It is apparent that in some instances more than one linker compound will bind to the ligand or receptor. A sufficient quantity of linker compound is employed to bind all or substantially all of the reactive functions of the ligand or receptor. For protein or other ligand or receptor for which structure is unknown one can titrate for sulfhydryl groups to determine the optimum ligand (receptor)/linker compound ratio. Specific examples set forth below illustrate further the coupling of linker compounds of Formulas I and II with ligands or receptors to form the appropriate intermediates represented by Formulas IV and V suitable for reaction with bacterial luciferase.

In the compounds of Formulas IV(a) and IV(b), $R_1$, $R_2$, $R_3$, $R_4$, $R_5$, $R_7$ and n have the meanings defined in Formulas I and II; m is an integer equivalent to the number of reactive functions present on the ligand or receptor capable of reacting with the linker compound and preferably is an integer of from 1 to 40; Y represents the ligand or receptor to be labeled or assayed absent the functional group which reacted with the linker compound; and X represents the functional linkage between the linker compound and the ligand or receptor and is

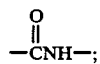

—NR wherein R is hydrogen or any group which may be present on the ligand or receptor functional secondary amine;

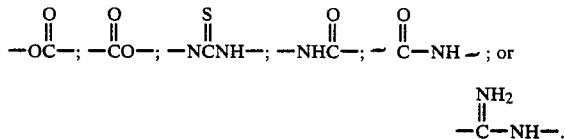

The intermediates of Formula IV(b) are a part of the present invention.

Once the linker compound-ligand and the linker compound-receptor intermediates are formed said intermediates are brought together with bacterial luciferase to effect thiolalkylation of the reactive sulfhydryl group of luciferase and the reactive $R_1S$—S— or the $R/S(O_2)$-S—moieties of the linker compounds of Formulas I and II respectively. The quantity of reactants employed varies with the number of sulfide or sulfoxide reactive groups available on intermediates and is controlled such that each such group binds a luciferase molecule. As the luciferase reacts with the linker compound-ligand or linker compound receptor intermediate the luciferase is inactivated. Therefore it is convenient to add to an excess of luciferase in a buffer, e.g., 0.2M phosphate buffer, pH 7.5, the intermediate of Formula IV(a) or IV(b) portion wise until there is a disappearance of enzyme activity. We have found that the addition of a nonionic surfactant or detergent such as polysorbate 80 or polyethylene glycol p-isoacetylenephenyl ether to the reaction medium may improve the assay sensitivity. This is believed to be related to the hydrophobicity of the region of the luciferase molecule wherein the reactive sulfhydryl group resides. As the carbon chain length of the linker compound increases the need to add a surfactant generally decreases, however, the presence of a nonionic surfactant in the reaction medium wherein any of the intermediates of Formula IV(a) or IV(b) is not detrimental. A final concentration of about 0.05% to 0.5%, preferably 0.05% to 0.1%, of surfactant in the reaction mixture is suitable. The luciferase labeled ligand or luciferase labeled receptor as depicted by Formula V may be separated from any unreacted intermediate by various known techniques, e.g., molecular seive solunn chromatography or ultrafiltration. In Formula V, $R_2$, $R_3$, $R_4$, $R_5$, n, m, X and Y are as defined in Formulas IV(a) and (b) and E is as depicted below in Formula VII.

In performing the assay the incubation medium containing the sample being assayed must be free of any reducing agent or must be determined and corrected for by using, e.g., methyl methanethiolsulfonate labeled luciferase in a control sample. If the free sulfhydryl levels in the sample to be tested are very high and producing a high background it may be advantageous to add a reducing agent scavenger to the test sample prior to assaying.

The assay incubation medium is buffered to a pH of about 6 to 9.5, and the buffer ideally contains a high concentration of anions such as phosphate, arsenate, citrate, sulfate, pyrophosphate. Usually the incubation medium will contain a high concentration of protein, but if not, protein, such as, bovine serum albumen (BSA), should be added. Generally 0.1 mg of BSA per ml of incubation medium is adequate. The temperature of the incubation medium can vary from about 0° to 40° C. but preferably is about room temperature, i.e., 25°-30° C. The incubation period varies with the ligand being assayed but is usually less than one hour. Of course, for prolonged incubation periods antibacterial agents such as EDTA could be added to the medium. Addition of a nonionic surfactant, e.g., as identified hereinabove, in the incubation medium may also be useful in improving the sensitivity of the assay for the reasons indicated hereinabove.

Following incubation and in those assay systems wherein either the ligand or the receptor is immobilized the incubation medium is decanted and the immobilized material is washed with a buffer solution of the type used in the incubation medium. In those assay systems wherein the ligand and receptor remain soluble the receptor-bound material is separated from the unbound material by various means commonly known in the art. For example, this separation can be achieved by treatment with polyethylene glycol [B. Desbuquois and G. D. Aurback, J. Clin. Endocrinol. Metab. 33, 732 (1971)]or IgG Sorb or by contacting the incubate with a second antibody. The second antibody, which is prepared by standard procedures, e.g., as described by Doughaday, et al., "Principles of Competitive Protein Binding Assay," J. B. Lippincott, Philadelphia (1971), is particularly preferred.

In those assay systems wherein more than one receptor is employed the conditions of the incubation medium and the separation techniques are substantially the same as described above with the additional receptors being added sequentially and at time intervals to permit binding of the various components involved.

Once the bound material is separated it is combined with a buffer of the type used in the incubation medium along with a sulfide reducing agent, such as, 0.1M β-mercaptoethanol, 0.01 to 0.05M dithiothreitol, 0.01 to 0.05M dithioerythritol or sodium dithionate, and protein (non-protease) such as BSA. The time require for reduction and recovery of active luciferase can be standardized for each ligand, and generally will be from one to 60 minutes. The luciferase is then activated by any one of the various known techniques, e.g., the dithionate method; or the flavin squirt or injection technique (J. W. Hastings, et al., Methods Enzymol. 57, 135-152 (1978); or the coupled assaying flavin reductase method (E. Jablonki and M. Deluca, Methods Enzymol. 57, 202–214 (1978); and P. E. Stanley, Methods Enzymol. 57, 215–222 (1978).

The light emitted by the luciferase can be measured by using a luminometer, a photomultiplier photometer, or a liquid scintillation counter, and by comparison to standard curves for known quantities of ligand or receptor the concentration of substance being measured in the sample is determined. Standard curves are generated by the foregoing procedure using known quantities of ligand or receptor.

The following represent preferred representative procedures for performing the immunoassay of the present invention.

Procedure I: Double antibody method

A. Immunoassay: A prepared sample (0.1 ml) is incubated with 0.1 ml of a first antibody or receptor and luciferase-labeled ligand (0.1 ml) for a period of time ranging from 5 to 20 minutes depending on the affinity of the receptor. Following incubation, 0.1 ml of a second antibody or receptor is added and the medium is incubated for an additional 30 minutes after which 2 ml of saline solution is added, and the mixture is centrifuged at 3000 G for 5 minutes. The pellet is resuspended in 0.94 ml dithiothreitol (20 mM) containing assay buffer (0.02M phosphate buffer, pH 7.0, with 0.2% bovine serum albumin and 20 mM dithiothreitol) and incubated for 30 minutes.

B. Detection of the bound ligand: Any one of the three methods to detect the luciferase activity as described hereinabove can be used, for example, using the methods described by J. W. Hastings, et al., Methods Enzymol. 57, 135–152 (1978). The unknowns are estimated against a standard curve which is established using the identical assay.

Procedure II: Solid phase method

The receptor can be attached onto a solid matrix, such as, *Staphylococci aureus*, microbeads, polyethylene/polystyrene tubes, by various known methods. See, Clark and Engvall, ibid.; Sheehan and Cruickshank, ibid.; and E. O'Keefe and B. Vann, J. Biol. Chem. 255, 561–568 (1980). The immunoassay procedures are designed according to the nature of solid matrix-receptor complex.

A. Receptor-coated beads or *S. aureus*

1. Immunoassay: 0.1 ml of prepared sample, 0.1 ml of luciferase labeled ligand, and 0.1 ml of the receptor-coated beads are incubated for a period of time as described above. At the end of the incubation, 2.0 ml of saline solution is added and then centrifuged at 3000 G for 15 minutes. The pellet is resuspended in the buffer and incubated as described above. Then the resuspension is centrifuged at 3000 G for 10 minutes and 0.5 ml of the supernatant is transferred to a new assay tube for detection.

2. Detection of bound ligand: 0.45 ml of the assay buffer is added to the 0.5 ml supernatant and the activity is detected as described above in Procedure I B. Receptor-coated tubes 1. Immunoassay: 0.1 ml of prepared sample, 0.1 ml of luciferase labeled ligand, and 0.3 ml of phosphate buffered saline solution are incubated for a period of time as described above. At the end of the incubation, 2.8 ml of saline solution is added, and the whole mixture is decanted, after which the assay buffer as described above is added and incubated. Detection of bound antigen is carried out as described above. The following specific examples further illustrate the invention.

EXAMPLE 1

Potassium methyl sulfonate

Hydrogen sulfide gas was passed through a stirred solution of 10 g (150 mm) of potassium hydroxide in 80 ml $H_2O$, cooled in an ice bath until the solution was saturated. While cooling in ice bath, there was added very slowly (syringe pump) over one hour 5.8 ml methane sulfonyl chloride (75 am). Stirring was continued for another hour, then the mixture was filtered and evaporated to dryness under reduced pressure. To the resultant residue was added 25 ml dimethyl formamide and the mixture was warmed to 60° C. with stirring for about 45 minutes under a nitrogen atmosphere. The mixture was then filtered, washed with DMF and dried under reduced pressure to give the title compound which was recrystallized from isopropyl alcohol.

EXAMPLE 2

3-(Methylsulfonylthio)propionic acid

One g (6.6 am) of homopropionic acid in 10 ml DMF was treated with 2.0 g (13 mm) of $CH_3SO_2SK$ with stirring under $N_2$ in a 60° C. oil bath for 4 hours. Upon cooling the mixture was diluted with $H_2O$, acidified in 2N $KHSO_4$, extracted with ethyl acetate, washed sequentially with ice cold $KHSO_4$, $H_2O$, then brine, dried over $Na_2SO_4$, and evaporated to give the title compound.

EXAMPLE 3

3-(Methylsulfonylthio)propylamine·HBr 1.74 g of 3-homopropylamine·HBr and 1.35 g of $CH_3SO_2SK$ in 5 ml DMF was stirred under $N_2$ at 60° C. for 3 hours, then filtered through Celite, washed in more DMF and evaporated using a viscous oil. The oil was combined with 7 ml of 1:1 acetonitrile-ether and stirred for one hour. The resulting precipitate was washed with ether, dried, dissolved in hot acetonitrile, filtered and cooled. Upon cooling a precipitate formed which was recrystallized from methanol-ethylacetate to give the title compound.

EXAMPLE 4

5-(Methylsulfonylthio)pentanoic acid

A mixture of 1g of 5-bromovaleric acid, 1 g of $CH_3SO_2SK$ and 10 ml DMF was stirred under $N_2$ at 60° C. for 3 hours. The mixture was then filtered, washed with DMF, and evaporated under reduced pressure to dry. The resulting residue was chromatographed on 100 g $CC_4$ packed in 50% EtOAc-Skellysolve B eluting with 1 1 100% EtOAc-Skellysolve B to give the title compound. M.P. 69°–71° C.

When in the above procedure 6-bromohexanoic acid or 4-bromobutanoic acid is substituted for 5-bromovaleric acid one obtains 6-(methylsulfonylthio)hexanoic acid, M.P. 71°–76° C., and 4-(methylsulfonylthio)butanoic acid respectively.

EXAMPLE 5

2-(Methylsulfonylthio)ethylamine·HBr

A mixture of 1.63 g of 2 bromoethylamine hydrobromide and 1.35 g of $CH_3SO_2SK$ in 5 ml DMF was stirred under $N_2$ at 60° C. for 3 hours. The mixture was then filtered through Celite, washed with DMF, and evaporated under reduced pressure to give an oil. The oil was combined with about 7 ml of 1:1 acetonitrile-ether solution and stirred for one hour, then chromatographed on 300 g CC$_4$ packed in 10% MeOH-EtOAc, and eluted with 3 1 10–50/5 MeOH-EtOAc to give the title compound. M.P. 109°–114° C. When in the foregoing procedure one substitutes 3-bromopropylamine. HBr for 2-bromoethylamine·HBr, the product obtained is 2-(methylsulfonylthio)propylamine.HBr.

EXAMPLE 6

(a) Estriol-6-(0)-carboxymethyl oxime (E$_3$-CMO) is prepared from estriol (1,3,5-estratrien-3,16α, 17β-triol) and carboxymethyloxime by known procedures. See F. Kohen, et al., "Preparation of Antigenic Steroid-Protein Conjugates" in Steroid Immunoassay, E. D. H. Cameron, S. C. Hiller, and K. Griffiths, eds., Alpha Omega Publishing Ltd., Cardiff (1975), pp. 11–32.

A solution of 5 mg of E$_3$-CMO in 0.2 ml of tetrahydrofuran is reacted with 2.5 mg of carbonyldiimidazole for 30 minutes at about 25° C. after which 3.85 mg of 5-(methylsulfonylthio)pentylamine is added. The pH of the reaction mixture is adjusted to 8.0 by the addition of 0.01 ml of 1.0 M aqueous sodium hydroxide. The reaction is permitted to proceed for 18–19 hours at about 25° C., and the product is isolated by thin layer chromatography using silica gel G and a 6:4 mixture of chloroform:methanol. The UV absorbing spots were scraped from the plate, eluted with chloroform:methanol (6:4) followed by THF:ethanol (5:5), then dried under nitrogen to give estriol-6-0[5-(methylsulfonylthio)pentylaminocarbonyl]methoxime, having Formula VI. The compound was identified by NMR and quantitated by UV at 262 nm.

(b) A mixture of 1.0 ml of luciferase from *Vibrio harveyi* (2.2×10$^{-6}$ M) having a weight extinction coefficiency of $$\epsilon^{0.1\%}_{280\ nm} : 10\ mm$$

of 0.94, in phosphate buffer 0.1 M, pH 7.5, containing 0.8% sodium chloride and 0.05% Tween 80 was reacted with 0.06 ml or 3.5×10$^{-5}$ M from 6(a) having a molar extinction coefficiency of $$\epsilon^{m}_{262\ nm} : 10\ mm$$

of 1.18×10$^{-4}$ [O.D. 262 nm=0.49 for 3.5×10$^{-3}$ M]. The reaction was carried out at about 25° C. for 30 minutes after which the reaction mixture was ultra filtered. The filtrate was diluted with 4.5 ml of phosphate buffer 0.02M, pH 7.0, to yield 7.7×10$^{-6}$ M of the product of Formula VII wherein E represents luciferase absent the reactive sulfhydryl group. When 0.1 ml of the product of Formula VII was incubated with 1.0 ml of buffer containing 0.02 M phosphate buffer, pH 7.0, 0.2% BSA and 20 mM dithiothreitol, the recovery of light as compared with the equivalentquantity of untreated luciferase was over 90%.

EXAMPLE 7

(a) Triiodothyronine methyl ester 325 mg of triiodothyronine was dissolved in 40 ml of dry methanol saturated with hydrogen chloride gas at room temperature. After complete dissolution, the mixture was allowed to stand overnight. The triiodothyronine methyl ester·HCl was precipitated by distillation under vacuum. The precipitate was filtered off, washed with alcohol and ether, then dried. The ester hydrochloride was dissolved in 5 ml of 80% ethanol and treated with 2N NaOH to neutral. Recrystallization of the ester was completed by addition of 5 to 10 ml H$_2$O and standing at 4° C. The crystals were then collected on a sintered glass funnel and dried in a dessicator under reduced pressure at 4° C. The recovery was about 80%. The resulting product of the reaction was separated by thin layer chromatography on silica gel G plate (methanol:triethylamine =90:10). UV absorbing material of Rf=0.56 was collected and (b) Coupling of triiodothyronine (T$_3$)-methyl ester to 4-(methylsulfonylthio)butanoic acid 150 mg T$_3$-methyl ester was neutralized with 4.0 ml of 0.133 N NaOH containing 0.5 ml of THF:DMF mixture (1:1) (37.5 mg/ml final concentration). A 0.03 ml (1.125 mg) portion of this mixture was introduced into a mixture containing 4-(methylsulfonylthio)butanoic acid (1.0 ag) and 1-ethyl-3,3-dimethylaminophenylcarbodiimide EDAC (1.0 mg) at pH 6.0 in 0.01 M phosphate buffer. The reaction was allowed to proceed at room temperature overnight. The resulting product was used as described in part (c) below without further purification.

(c) Conjugation of product of Formula VIII with luciferase

Inhibition of luciferase forming the product of Formula IX wherein E has the meaning defined above was carried out mixing the product of Formula VIII with luciferase under the following conditions (Product of Formula VIII 3.5×10$^{-5}$ M:luciferase 2.2×10$^{-6}$ M in 0.1 M, phosphate buffer, pH 7.5, with 0.8% NaCl and 0.05% Tween 80.) The reaction mixture after 30 minutes was diluted with 0.02M phosphate buffer at pH 7.0 to 4.5 ml.

EXAMPLE 8

Immune reaction 0.5 ml rabbit anti-T$_3$ antiserum was mixed with 10 ml of 10% suspension of IgGsorb (*S. aureus* Cowan I inactivated particles in 0.9% NaCl). The mixture after 2 hours at room temperature was washed with 0.9% NaCl extensively, and reconstituted to the original volume (10 ml). A 0.2 ml portion of this suspension was used as solid phase antibody suspension, to which 0.1 ml of the solution from Example 7(c) (product of Formula IX) was added and incubated at room temperature for 2 hours. The reaction mixture was centrifuged and washed with 1 ml of phosphate buffered saline (pH 7.5 0.01M phosphate), and 20 mM (final) of dithiothreitol (DTT) was added. Control assay was carried out with *S. aureus* beads absorbed with normal rabbit serum.

After reaction with dithiothreitol, the reaction mixture was centrifuged 3000 G for 5 minutes. The supernatant was assayed for the presence of luciferase as an indicator for triiodothyronine. There was a significant difference in light emission between antibody-*S. aureus* particles and normal rabbit serua-*S. aureus*-particle. This indicates that anti-T$_3$ recognized the product of Formula VIII.

| Reaction with T$_3$ luciferase | Light emission |
| --- | --- |
| Ra-anti T$_3$-*S. aureus* | 28 mV × 10 multiplication factor |

-continued

| Reaction with $T_3$ luciferase | Light emission |
| --- | --- |
| Normal-Ra-serum-*S. aureus* | 7 mV × 10 multiplication. |

EXAMPLE 9

Luminescence-enzyme-immunoassay (a) 0.1 ml of the product of Formula VII (specific activity:4~6 mV/pg, 1~1.5 V/0.1 ml) obtained in Example 6(b) and 0.9 ml of phosphate buffer 0.1M, pH 7.0, containing 0.88% NaCl (PBS) are incubated in tubes coated with anti-estriol antibodies at room temperature for 1.0 hour after which 2 ml of saline is added and the whole liquid is decanted. Then 1.0 ml of the assay buffer (0.02 M phosphate buffer, pH 7.0, with 0.2% BSA and 20 mM DTT) is added and incubated at room temperature for 15 minutes. The luciferase activity is measured using FMNH-injection method. A comparable control is performed by the identical method except using a blank tube not coated with antibody.

(b) 0.1 ml of the product of Formula IX (1.5–2.0 mV/pg, 200–400 mV/0.1 ml), 0.1 ml of PBS and 0.1 ml of anti-$T_3$ antibodies immobilized on *S. aureus* at room temperature for two hours. At the end of the incubation, the reaction mixture is washed twice with 2.0 ml saline by resuspension and centrifugation. Then 1.0 ml of the assay buffer as described above is added and incubated at room temperature for 15 minutes. The *S. aureus* are spun down and the supernatant is transferred to an assay tube for the measurement of luciferase activity by the FMNH-injection method.

EXAMPLE 10

$T_4$-Thyroxine-$C_5$ acid-luciferase conjugate

To a solution of 20 mg ($8.62 \times 10^{-2}$ mmole) of 6-(methylsulfonylthio)hexanoic acid in 5.0 ml ethanol, 5.0 ml 0.20M phosphate, pH 4.5, and 2.0 ml water was added 17 mg ($8.62 \times 10^{-2}$ mmole) of EDAC. The mixture was stirred for 30 minutes during which time the pH maintained at 4.5 after which 68 mg ($8.62 \times 10^{-2}$ mmole) of thyroxine methyl ester was added. The pH of the reaction mixture was raised to 8.5 using 1.0 N aqueous NaOH and maintained for three hours. The resulting product was extracted with ethyl acetate (10 ml, 3X), and the extracts were dried on a rotovap. The residue was resuspended in 3 ml of ethanol and stored at $-10°$ C. for 48 hours whereupon a precipitate formed giving the product of Formula X.

EXAMPLE 11

$T_4$-assay

An inactivation of mixture of 100 μl of luciferase (at $8.0 \times 10^{-7}$ M) and 3 μl of the product of Formula X in dimethylformamide (DMF) was incubated for 12 minutes. A control mixture of 100 μl of luciferase (at $8.0 \times 10^{-7}$ M) and 3 μl of DMF was also incubated. The inactivation mixture and the control mixture were added to separate plastic tubes coated with anti-thyroxine (anti-$T_4$) antibody and containing 1.0 ml of 20 mM phosphate and 0.2% BSA, pH 7.0) to give a final volume of 1.1 ml. The mixtures were incubated for one hour at 37° C. with occasional stirring after which each was washed with two 1.0 ml volumes of 10 mM phosphate, pH 7.0. Following the washing step 1.0 ml of 10 mM phosphate and 20 μl of 10 mM β-mercaptoethanol (β-ME) was added to each of the inactivation sample and the control sample. Also 20 μl of β-ME was added to each of the washes. Each sample and the washes were incubated for 60 minutes at about 22° C. after which each was assayed for luciferase activity. There was no observed enzyme activity in any of the washes or the control sample. There was an observed 0.0182 light units (LU) in the inactivation sample or an efficiency of $2.2 \times 10^{-3}$% based on the following assumptions: (1) The known activity of luciferase is $\sim 1.25 \times 11 \rlap{=}{\neq} $LU/μmole of enzyme and 1 LU$\cong 1 \times 10^{10}$ quanta/sec.; (2) The amount of anti-$T_4$ antibody per tube was about 100 μg or about $6.67 \times 10^{-4}$ μmole; (3) There was a 1:1 stoichometry of antibody to antigen; and (4) The maximum detectable LU was ($6.67 \times 10^{-4}$ μmole)($1.25 \times 10^{\rlap{=}{\neq}}$LU/μmole)=834.

EXAMPLE 12

Progesterone-$C_3$amine-intermediate

To a solution of 35.4 mg (0.08 mmole) of 11α-progesterone hemisuccinate in 8 ml of dimethylformamide, 5 ml water, and 0.30 ml 1.00 M phosphate, pH 7.0, was added 15.4 mg (0.08 mmole) of EDAC. The pH of the mixture was adjusted to 5.1 with 1.0 NHCl. The mixture was stirred at room temperature for ½ hour maintaining the pH at 5.1 after which 20 mg (0.08 mole) of 3-(methylsulfonylthio)propylamine.HBr was added. Maintaining a pH of 8.0 the reaction was permitted to proceed for 90 minutes at 22° C., then the mixture was evaporated to dryness on a rotovap. The resulting residue was taken up in 3 ml of ethanol and stored at $-10°$ C. The product, as depicted by Formula XI, was purified on a $C_{18}$ reverse phase HPLC column. The ethanol soluble material was applied to the column in 20% ethanol/80% water. Luciferase inactivating activity was eluted to the end of a solvent gradient to 100% ethanol. All of the luciferase activity was recovered upon addition of β-ME.

EXAMPLE 13

Progesterone assay

An inactivation mixture of 100 μl of luciferase (at $8.0 \times 10^{-7}$M in 10 mM phosphate, pH 7.0, 22° C.) and 2 μl of purified product of Formula XI was incubated for about three minutes after which 1.0 ul of anti-progesterone antibody was added and incubation was continued for three minutes. Following the second incubation 2 mg of protein A-sepharose was added and the medium was incubated another three minutes with moderate agitation. The medium was then centrifuged. The pellet and supernatant were separated. The supernatant was retained for enzyme content analysis. The pellet was washed with three 100 μl volumes of 10 mM phosphate buffer, pH 7.0. Following the wash step 2 μl of β-ME was added to each of the washes, the supernatant, and the pellet then each was assayed for luciferase activity. Most of the enzyme activity (98.4%) was recovered from the supernatant. From the first wash about 0.4% enzyme activity was recovered; no activity was found in the second wash; and 1% of the enzyme activity was recovered from the pellet.

As a control to demonstrate the viability of the enzyme integrity 100 μl of luciferase ($8.0 \times 10^{-7}$ M, 10 mM phosphate, pH 7.0) and 2 μl of the product of Formula XI in ethanol ($6.4 \times 10^{-7}$ M) were combined whereupon about 80% of the enzyme activity was lost within 10 minutes. Addition of 2 μl of β-ME resulted in recovery of 90% of the initial activity within two minutes.

Also to demonstrate the stability of luciferase in the presence of antibody and protein A-sepharose 100 μl of luciferase ($8.0 \times 10^{-7}$M) (10 mM phosphate, pH 7.0) and 5 mg of lyophilized protein A-sepharose were combined and there was no observed effect on enzyme activity. Similarly 100 μl of luciferase ($8.0 \times 10^{-7}$M) (10 mM phosphate, pH 7.0) and 1 μl of anti-progesterone antibody were combined and no effect on luciferase activity was observed after 50 minutes.

EXAMPLE 14

Insulin-C₃amine-luciferase conjugate (a) A mixture of 20 μl ($1.75 \times 10^{-4}$ mmoles) of porcine insulin (having about 5 moles of carboxyl groups per mole of protein), 10 μl EDAC ($1.4 \times 10^{-3}$ mmoles) and 7.74 ml of 50 mM phosphate buffer, pH 4.7, was reacted for about one hour at 22° C. after which 2.0 ml of 3-(methylsulfonylthio)propylamine·HBr ($1.6 \times 10^{-3}$ mmoles) in ethanol was added. The pH of the mixture was adjusted to 8.2 and the reaction was allowed to proceed for 6 hours at 22° C. whereupon the mixture was transferred to a spectrapore 6 dialysis tubing (1000 m.w. cut off) and dialyzed against 500 ml of 50 mM phosphate buffer, pH 7.1 at 4° C. for 16 hours to give the insulin C₃amine intermediate.

A 100-fold excess of the above-obtained intermediate (88 μM) and luciferase in 10 mM phosphate buffer, pH 7.0, were incubated at 22° C. for about 8 minutes to give the insulin-C₃amine-luciferase conjugate.

EXAMPLE 15

The conjugate obtained nn Example 14 is used to determine the concentration of cell surface insulin receptors in rat hepatoma cells as follows. The cell lines, buffers and reagents are prepared as described by procedures known in the art. See, J. F. Ballard, et al., J. Cell Physio. 105, 335-336 (1980) and J. M. Gunn, et al., J. Cell Physio., In Press.

The insulin C₃-amine luciferase conjugate is added to a monolayer of RH35 hepatoma cells in 100 μM TES, pH 7.85, with Earl's Balanced Salts for a final concentration of 0.1-10 nM. A control mixture is prepared in the identical manner except that unlabeled insulin for a final concentration of 0.1-1 μM is employed. Each of the mixtures is washed 3 times with volumes of PBS equivalent to that of each mixture after which β-mercaptoethanol is added to a final concentration of 0.05-0.2 M to each of the wash volumes and the final experimental and control monolayer mixtures. After 60 minutes at about 22° C. each wash or mixture is assayed for luciferase activity using the flavin injection method to determine the concentration of recettors.

EXAMPLE 16

Estriol (E₃) standard curve 0.1 ml of estriol-luciferase product of Formula VII in 0.1M phosphate buffer, pH 7.0, with 0.05% Tween 80 plus 0.1 ml phosphate buffer, pH 7.0, containing 0.05% Tween and 0.85% NaCl plus 0.1 ml of E₃ standard plus 0.1 ml primary antibody solution containing 1/300 diluted sheep anti-E₃, 1/60 diluted normal sheep serum in 0.1M PBS, pH 7.0, with 0.05% Tween 80. The mixture was incubated at room temperature for 60 minutes, then 0.1 ml of secondary antibody solution (4.8% polyethylene glycol and 1/2.5 diluted donkey-anti-sheep antibody in the PBS buffer described above). The mixture was incubated for an additional 30 minutes and then centrifuged at 2500×G for 15 minutes. The supernate was decanted and the pellet was resuspended in 0.2 ml dithiothreitol solution (10 mM) and incubated at room temperature for another 15 minutes. Then 0.72 ml of the assay buffer (as described above) was added and the luciferase activity was determined by the FMNH₂-injection method. The standard curve then was constructed with B/Bo of 59%, 42%, and 36% for 50, 250 and 500 pg estriol/tube. A linear standard curve was obtained over the range stated on a loglogit scale.

FORMULA CHART

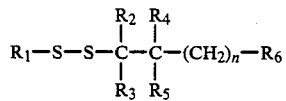

Formula I

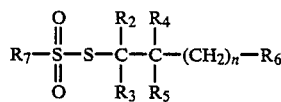

Formula II

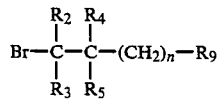

Formula III

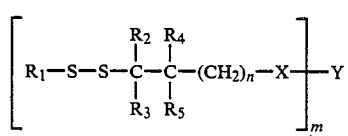

Formula IV(a)

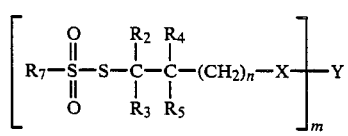

Formula IV(b)

-continued
FORMULA CHART
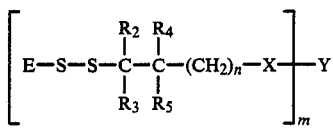
Formula V
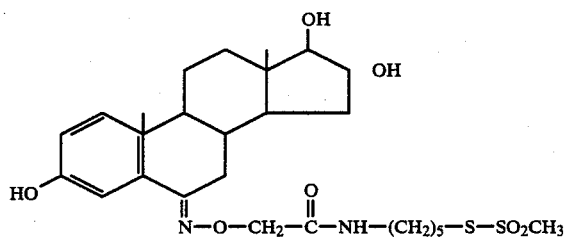
Formula VI
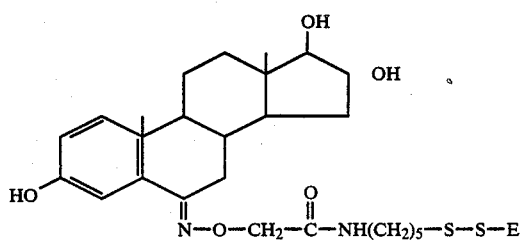
Formula VII
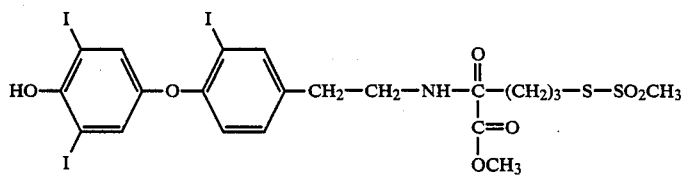
Formula VIII
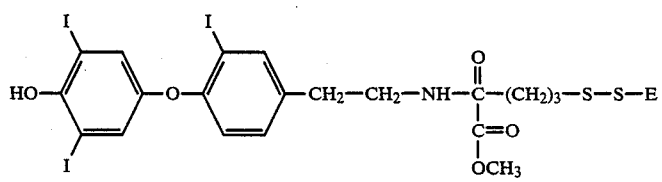
Formula IX
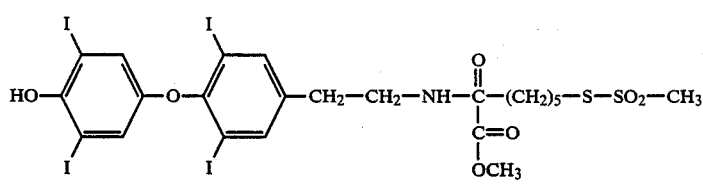
Formula X
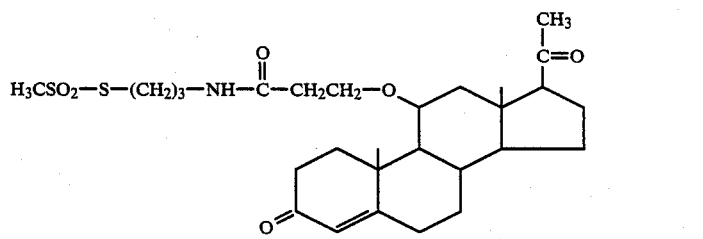
Formula XI
We claim:
1. A compound of the formula
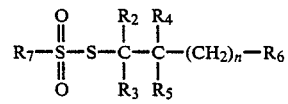

wherein R₇ is a lower alkyl group having from 1 to 6 carbon atoms; phenyl; phenyl substituted with fluoro, nitro or a lower alkyl group having from 1 to 4 carbon atoms; 2-pyridyl; or 4-pyridyl; n is zero to 15; is —COOH; —COOsuccinimide; —COCl; —COBr; Br;SCN; CN; 4-cyanophenyl;

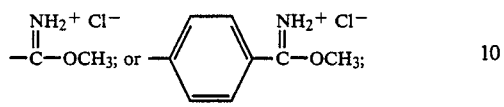

$R_2$ and $R_3$ are and are hydrogen, methyl or ethyl; $R_4$ and $R_5$ are the same and are hydrogen, methyl or ethyl; or $R_2$, $R_3$, $R_4$ and $R_5$ taken together with the carbon atoms to which they are attached represent a cycloalkyl group having from 4 to 6 carbon atoms, or represent 1,4-phenylene with the proviso that when $R_7$ is a lower alkyl group having one carbon atom or phenyl substituted with a lower alkyl group having one carbon atom and n is zero and each of $R_2$, $R_3$, $R_4$ and $R_5$ is hydrogen, $R_6$ is other than —NH₂.

2. A linker-compound-ligand or a linker-compound-receptor of the formula

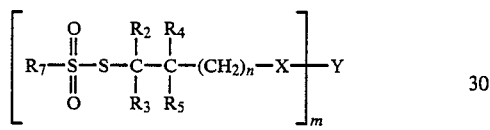

wherein $R_7$ is a lower alkyl group having from 1 to 6 carbon atoms; phenyl; phenyl substituted with fluoro, nitro or a lower alkyl group having from 1 to 4 carbon atoms; 2-pyridyl; or 4-pyridyl; n is zero to 15;

$R_2$ and $R_3$ are the same and are hydrogen, methyl or ethyl;

$R_4$ and $R_5$ are the same and are hydrogen, methyl or ethyl; or $R_2$, $R_3$.

$R_4$ and $R_5$ taken together with the carbon atoms to which they are attached represent a cycloalkyl group having from 4 to 6 carbon atoms, or represent 1,4-phenylene with the proviso that when $R_7$ is a lower alkyl group having one carbon atom or phenyl substituted with a lower alkyl group having one carbon atom and n is zero and each of $R_2$, $R_3$, $R_4$ and $R_5$ is hydrogen, m is an integer equivalent to the number of reactive functions present on the ligand or receptor capable of reacting with the linker compound;

X represents the functional linkage between the linker compound and the ligand or receptor and is

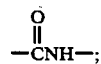

—NR— wherein R is hydrogen or any group which may be present on the ligand or receptor functional secondary amine;

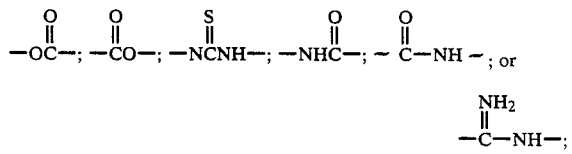

Y represents the ligand or receptor to be labeled or assayed absent the functional group which reacted with the linker compound.

* * * * *